United States Patent
Romero et al.

(10) Patent No.: US 9,498,620 B2
(45) Date of Patent: Nov. 22, 2016

(54) LEADS CONTAINING SEGMENTED ELECTRODES WITH NON-PERPENDICULAR LEGS AND METHODS OF MAKING AND USING

(71) Applicant: BOSTON SCIENTIFIC NEUROMODULATION CORPORATION, Valencia, CA (US)

(72) Inventors: Daniel James Romero, Granada Hills, CA (US);
(Continued)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/286,940

(22) Filed: May 23, 2014

(65) Prior Publication Data
US 2014/0353001 A1    Dec. 4, 2014

Related U.S. Application Data

(60) Provisional application No. 61/829,908, filed on May 31, 2013.

(51) Int. Cl.
*A61N 1/05*    (2006.01)
*H01R 43/26*    (2006.01)
(Continued)

(52) U.S. Cl.
CPC ........... *A61N 1/0534* (2013.01); *A61N 1/0551* (2013.01); *H01R 13/02* (2013.01); *H01R 43/26* (2013.01);
(Continued)

(58) Field of Classification Search
CPC .................................................. A61N 1/0534
(Continued)

(56) References Cited

U.S. PATENT DOCUMENTS 4,602,624 A    7/1986   Naples et al.
4,630,611 A    12/1986   King
(Continued)

FOREIGN PATENT DOCUMENTS

EP    0580928 A1    2/1994
EP    0650694 B1    7/1998
(Continued)

OTHER PUBLICATIONS

U.S. Appl. No. 14/286,889, filed May 23, 2014.
(Continued)

*Primary Examiner* — Stanley Tso
(74) *Attorney, Agent, or Firm* — Lowe Graham Jones PLLC; Bruce E. Black

(57) ABSTRACT

A method of making an electrical stimulation lead method includes attaching a pre-electrode to a lead body. The pre-electrode is a single, unitary, undifferentiated construct with a ring-shaped exterior. The method further includes attaching a plurality of conductor wires to the pre-electrode; and, after coupling to the lead body, removing an outer portion of the pre-electrode to separate remaining portions of the pre-electrode into a plurality of segmented electrodes spaced around the circumference of the lead body. When separated, each of the segmented electrodes includes a body and at least one leg extending inwardly from the body. The body defines an external stimulating surface and each of the at least one leg has an outer surface. For at least one of the at least one leg, the outer surface of the leg forms a non-perpendicular angle with the external stimulating surface of the body.

19 Claims, 9 Drawing Sheets

(72) Inventors: William George Orinski, Reno, NV (US); Joshua Dale Howard, Chatsworth, CA (US)

(51) Int. Cl.
*H05K 13/00* (2006.01)
*H01R 13/02* (2006.01)

(52) U.S. Cl.
CPC .......... *H05K 13/00* (2013.01); *Y10T 29/49174* (2015.01)

(58) Field of Classification Search
USPC ........................................................ 606/32
See application file for complete search history.

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,135,081 A | 8/1992 | Watt et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,391,985 B2 | 3/2013 | McDonald |
| 8,583,237 B2 | 11/2013 | Bedenbaugh |
| 8,649,873 B2 | 2/2014 | Moffitt et al. |
| 8,868,206 B2 * | 10/2014 | Barker et al. ................. 607/116 |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 * | 10/2008 | Jensen et al. ................. 607/119 |
| 2009/0204192 A1 | 8/2009 | Carlton et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 * | 4/2011 | Pianca et al. ................. 29/882 |
| 2011/0110386 A1 * | 5/2011 | Williams et al. ............... 372/12 |
| 2011/0130803 A1 | 6/2011 | McDonald |
| 2011/0130816 A1 | 6/2011 | Howard et al. |
| 2011/0130817 A1 * | 6/2011 | Chen ................... A61N 1/0534 607/116 |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0039590 A1 | 2/2014 | Moffitt et al. |
| 2014/0123484 A1 | 5/2014 | Digiore et al. |
| 2014/0142671 A1 | 5/2014 | Moffitt et al. |
| 2014/0155971 A1 | 6/2014 | Pianca et al. |
| 2014/0180375 A1 | 6/2014 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2008/100841 A1 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 14/286,934, filed May 23, 2014.

(56) References Cited

OTHER PUBLICATIONS

U.S. Appl. No. 14/286,829, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,797, filed May 23, 2014.
U.S. Appl. No. 14/469,214, filed Aug. 26, 2014.
U.S. Appl. No. 14/557,211, filed Dec. 1, 2014.
International Search Report and Written Opinion for PCT/US2014/039456 mailed Dec. 9, 2014.

* cited by examiner

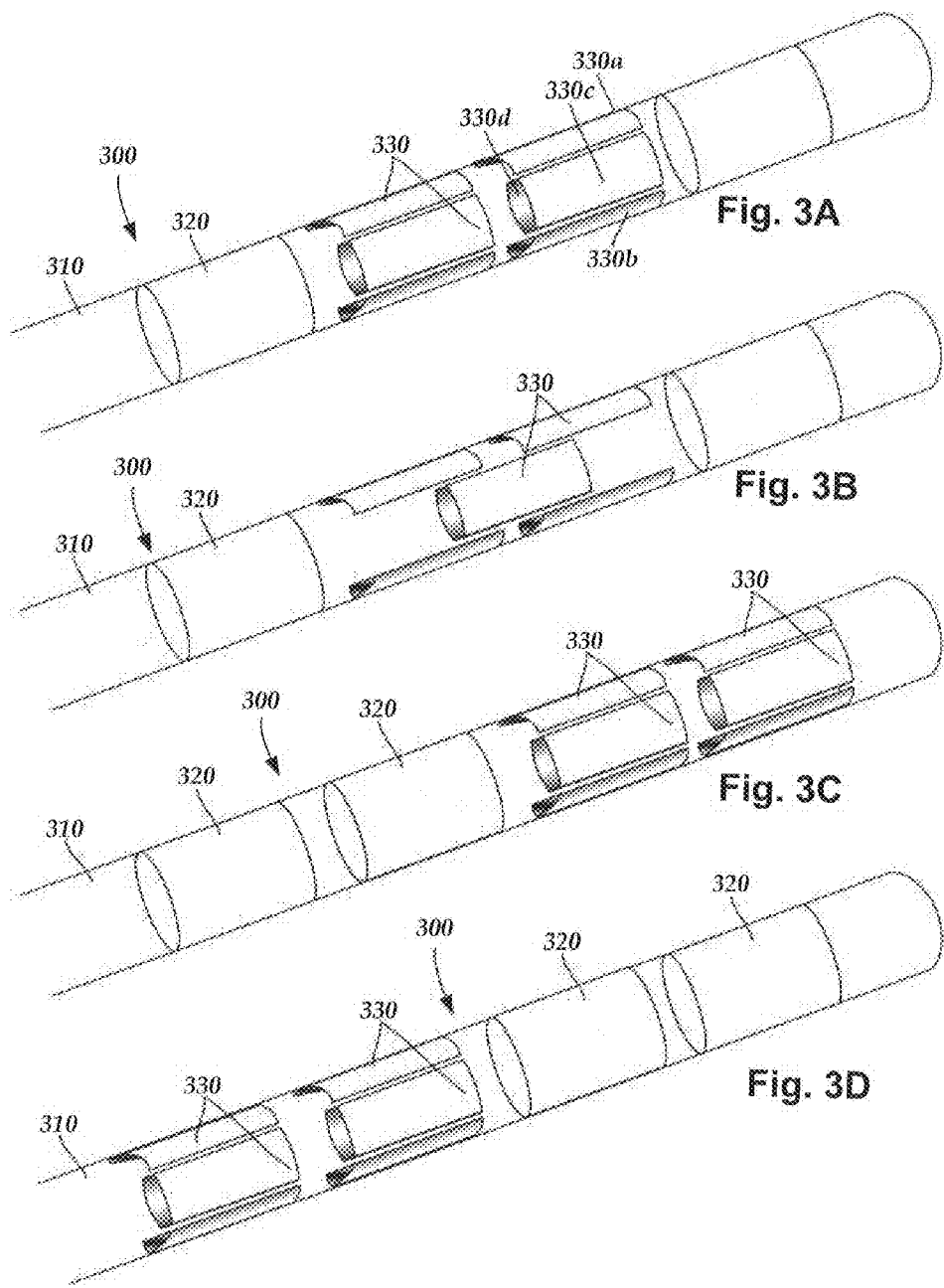

LEADS CONTAINING SEGMENTED ELECTRODES WITH NON-PERPENDICULAR LEGS AND METHODS OF MAKING AND USING

CROSS-REFERENCE TO RELATED APPLICATIONS

This application claims the benefit under 35 U.S.C. §119(e) of U.S. Provisional Patent Application Ser. No. 61/829,908, filed May 31, 2013, which is incorporated herein by reference.

FIELD

The present invention is directed to the area of implantable electrical stimulation systems and methods of making and using the systems. The present invention is also directed implantable electrical stimulation leads having segmented electrodes, as well as methods of making and using the leads and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a method of making an electrical stimulation lead. The method includes attaching a pre-electrode to a lead body. The pre-electrode is a single, unitary, undifferentiated construct with a ring-shaped exterior. The method further includes attaching a plurality of conductor wires to the pre-electrode; and, after coupling to the lead body, removing an outer portion of the pre-electrode to separate remaining portions of the pre-electrode into a plurality of segmented electrodes spaced around the circumference of the lead body. When separated, each of the segmented electrodes includes a body and at least one leg extending inwardly from the body. The body defines an external stimulating surface and each of the at least one leg has an outer surface. For at least one of the at least one leg, the outer surface of the leg forms an acute angle with the external stimulating surface of the body.

Another embodiment is a method of making an electrical stimulation lead. The method includes attaching a pre-electrode to a lead body. The pre-electrode is a single, unitary, undifferentiated construct with a ring-shaped exterior. The method further includes attaching a plurality of conductor wires to the pre-electrode; and, after coupling to the lead body, removing an outer portion of the pre-electrode to separate remaining portions of the pre-electrode into a plurality of segmented electrodes spaced around the circumference of the lead body. When separated, each of the segmented electrodes includes a body and at least one leg extending inwardly from the body. The body defines an external stimulating surface and each of the at least one leg has an outer surface. For at least one of the at least one leg, the outer surface of the leg forms an obtuse angle with the external stimulating surface of the body.

A further embodiment is a pre-electrode including an outer portion; and a plurality of segmented electrodes distributed around a circumference of the pre-electrode and within the outer portion. The pre-electrode is a single, unitary, undifferentiated construct with a ring-shaped exterior and is configured and arranged so that removal of the outer portion results in the remaining portions forming a plurality of separated segmented electrodes. Each of the separated segmented electrodes has a body and at least one leg extending inwardly from the body, the body defining an external stimulating surface and each of the at least one leg has an outer surface. For at least one of the at least one leg, the outer surface of the leg forms a non-perpendicular angle with the external stimulating surface of the body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a perspective view of an embodiment of a portion of a lead having a plurality of segmented electrodes, according to the invention;

FIG. 3B is a perspective view of a second embodiment of a portion of a lead having a plurality of segmented electrodes, according to the invention;

FIG. 3C is a perspective view of a third embodiment of a portion of a lead having a plurality of segmented electrodes, according to the invention;

FIG. 3D is a perspective view of a fourth embodiment of a portion of a lead having a plurality of segmented electrodes, according to the invention;

DETAILED DESCRIPTION

The present invention is directed to the area of implantable electrical stimulation systems and methods of making and using the systems. The present invention is also directed to implantable electrical stimulation leads having segmented electrodes, as well as methods of making and using the leads and electrical stimulation systems.

A lead for deep brain stimulation can include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads.

Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2011/0316615; 2013/0105071; and 2013/0197602, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead can include both recording electrodes and stimulation electrodes or electrodes can be used for both recording and stimulation.

Figure 1:
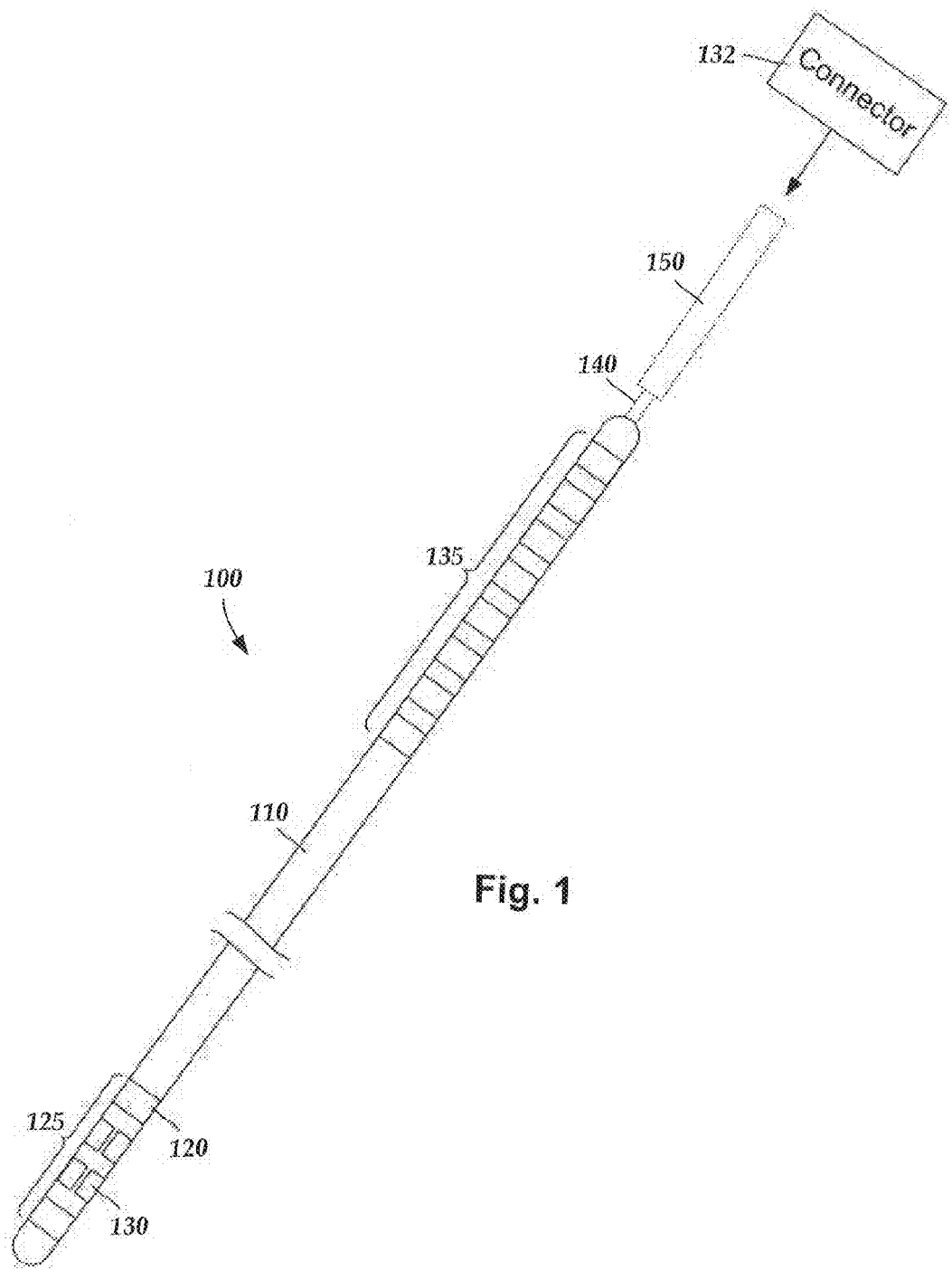
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator can have more or fewer than eight stimulation channels (e.g., 4-, 6-, 16-, 32-, or more stimulation channels). The control unit can have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 can be disposed on any part of the lead body 110, usually near a distal end of the lead 100. In FIG. 1, the lead 100 includes two ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes can be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320*a* of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

The lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two sets of ring electrodes 120 and two sets of segmented electrodes 130, the ring electrodes 120 can flank the two sets of segmented electrodes 130 (see e.g., FIG. 1). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). One of the ring electrodes can be a tip electrode (see, tip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Figure 3E:
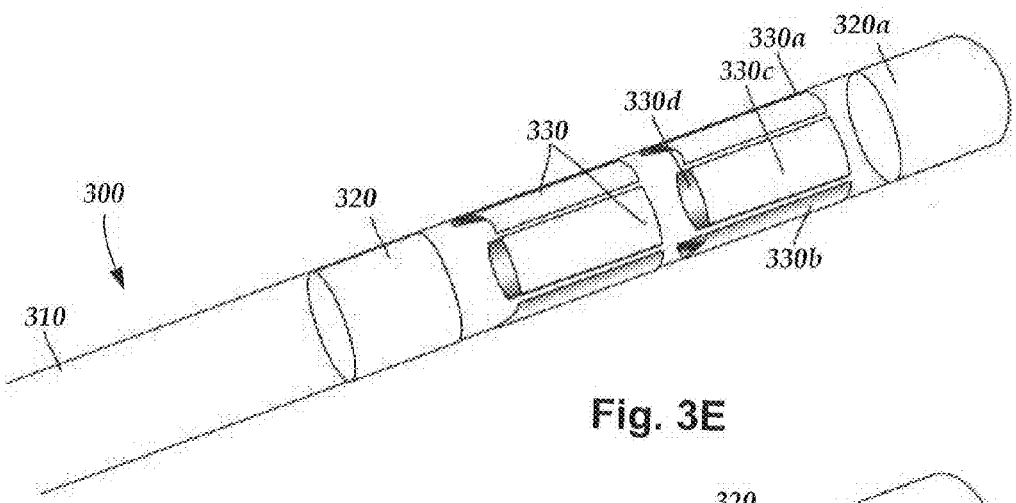
FIG. 3E is a perspective view of a fifth embodiment of a portion of a lead having a plurality of segmented electrodes, according to the invention.
Figure 3F:
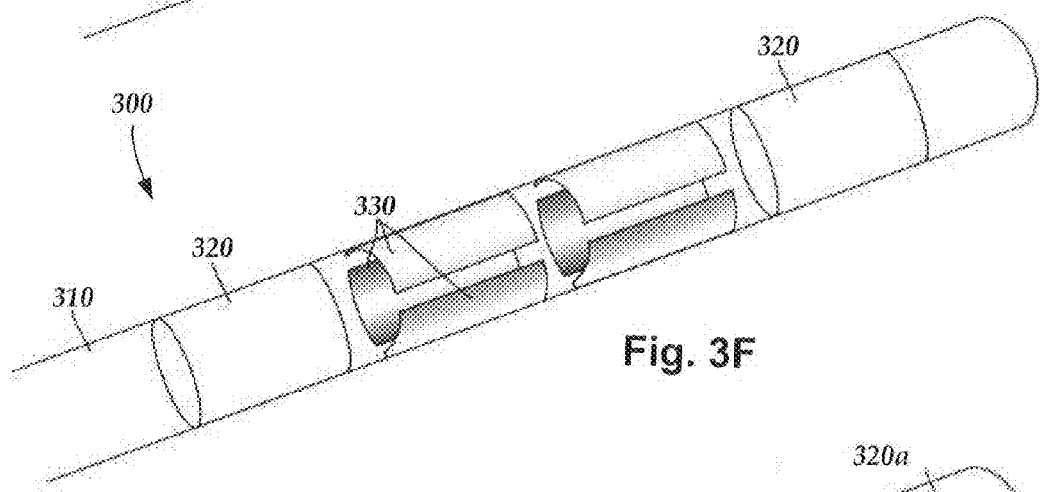
FIG. 3F is a perspective view of a sixth embodiment of a portion of a lead having a plurality of segmented electrodes, according to the invention.
Figure 3G:
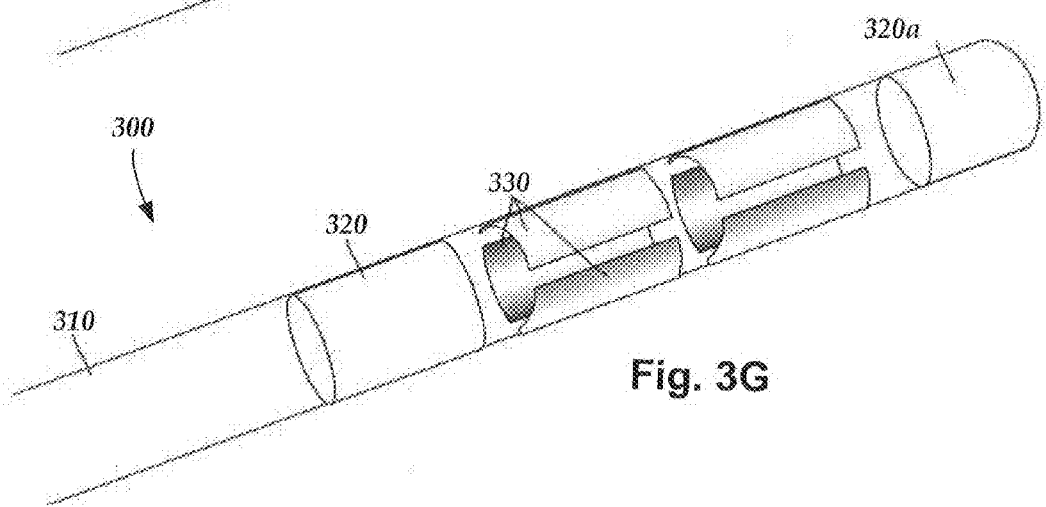
FIG. 3G is a perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E). It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F and 3G can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F and 3G has two sets of segmented electrodes, each set containing three electrodes disposed around the circumference of the lead, flanked by two ring electrodes (FIG. 3F) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
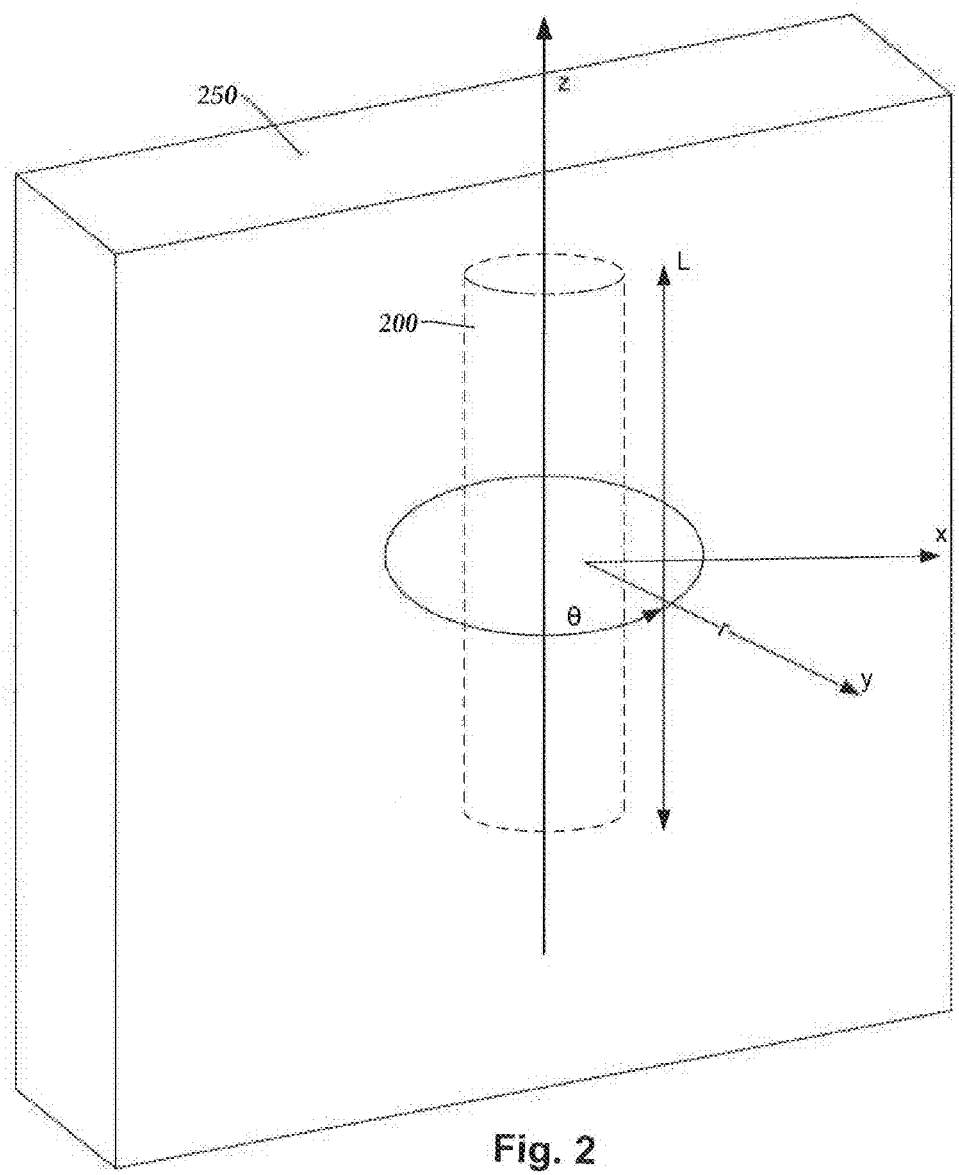
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identity the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered (see, FIG. 3B) relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

FIGS. 3A-3E illustrate leads 300 with segmented electrodes 330, optional ring electrodes 320 or tip electrodes 320a, and a lead body 310. The sets of segmented electrodes 330 include either two (FIG. 3B) or four (FIGS. 3A, 3C, and 3D) or any other number of segmented electrodes including, for example, three, five, six, or more.

Any other suitable arrangements of segmented electrodes can be used. As an example, arrangements in which segmented electrodes are arranged helically with respect to each other. One embodiment includes a double helix.

One challenge to making leads with segmented electrodes is the correct placement of the electrodes, and retention of the desired electrode placement, during the manufacturing process. In at least some embodiments, each segmented electrodes has one or more legs extending from an electrode body, where the outer surfaces of the leg and electrode body form a non-perpendicular angle. The non-perpendicular angle can be an acute angle or an obtuse angle. Further discussion of the acute and obtuse angles, with exemplary ranges or bounds, are provided below and are applicable to all embodiments disclosed herein unless otherwise indicated.

Figure 4A:
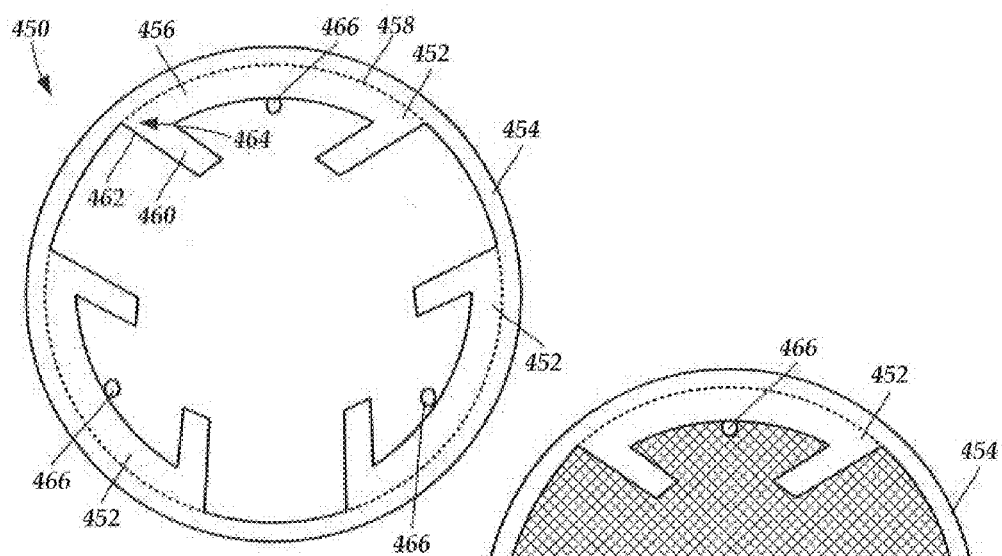
FIG. 4A is a cross-sectional view of one embodiment of a pre-electrode, according to the invention.

In at least some embodiments, the segmented electrodes can be formed using a pre-electrode with an outer portion that can be removed so that the remaining portions form the segmented electrodes. As an example, FIG. 4A illustrates a pre-electrode 450 having multiple segmented electrodes 452 that are connected together by a removable ring 454. The pre-electrode 450 of FIG. 4A has three segmented electrodes, but it will be understood that the pre-electrode, or any other pre-electrode described herein, can have any number of segmented electrodes including, but not limited to, two, three, four, five, or six or more segmented electrodes. The pre-electrode 450 of FIG. 4A has the segmented electrodes uniformly space-apart around the circumference of the pre-electrode, but it will be understood that in other embodiments, the spacing between segmented electrodes need not be uniform. The availability of uniform or non-uniform spacing of segmented electrodes is also applicable to all other pre-electrodes described herein.

In this illustrated embodiment (as well as the illustrated embodiments of FIGS. 7A-7C, 8A-8C, and 9A), the segmented electrodes 452 and ring 454 are formed of a single, unitary body. The ring 454 and segmented electrodes 452 are undifferentiated from each other in the pre-electrode 450. Because of the unitary nature of the pre-electrode, the ring and segmented electrodes are formed of the same material. The pre-electrode may be, for example, stamped, molded, or otherwise formed.

Each of the segmented electrodes 452 has an electrode body 456 and one or more legs 460 extending from the electrode body 456. The illustrated embodiment has two legs, but it will be understood that any number of legs can be provided including a single leg.

The electrode body 456 has an outer surface 458 (represented by the dotted lines in FIGS. 4A and 4B) that will be exposed when the ring 454 is removed during manufacture (see FIG. 4C) as described in detail below. In addition, each of the legs 460 has an outer surface 462. The outer surface 458 of the electrode body 456 forms an acute angle 464 with the outer surface 462 of the leg 460. In at least some embodiments, the acute angle is in the range of 25 to 85 degrees or in the range of 45 to 80 degrees. In at least some embodiments, the acute angle is no greater than 80, 75, 70, or 65 degrees. When the segmented electrode has two or more legs, the acute angles between the each individual leg and the electrode body can be the same or they can be different.

The segmented electrodes 452 can be formed in any suitable shape or size and can be formed of the materials described above. The description of this segmented electrode 452 is also applicable to all other segmented electrodes presented herein. Additional examples of segmented electrodes, including segmented electrodes that can be modified so that the leg(s) of those segmented electrodes form an acute angle with the electrode body, can be found in U.S. Provisional Patent Application Ser. No. 61/829,918, filed May 31, 2013, incorporated herein by reference.

In at least some embodiments, when separated from the ring 454 the outer surface 458 of the segmented electrode 452 has a curved shape. The curved shape preferably corresponds to the curvature of the lead. For example, the curved shape of the segmented electrodes can have an arc of at least 10, 15, 20, 30, 40, 50, or 60 degrees. The arc of the segmented electrode may be no more than 175, 160, 150, 125, 115, 100, or 90 degrees. In some instance, the arc of the segmented electrodes is in the range of 10 to 175 degrees or in the range of 30 to 120 degrees or in the range of 40 to 100 degrees. The illustrated embodiments include three electrodes 452 disposed in the ring 454, but it will be recognized that any number of electrodes could be disposed within the ring including two, four, five, six, or more electrodes.

Figure 5:
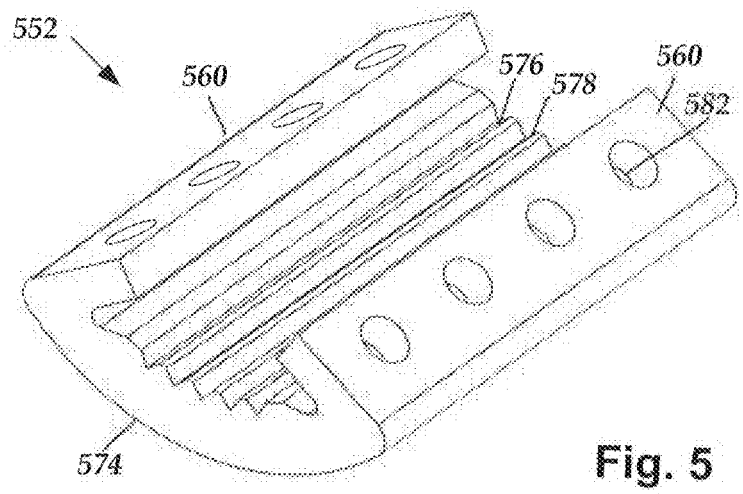
FIG. 5 is a perspective view of one embodiment of segmented electrode, according to the invention.

FIG. 5 illustrates one embodiment of a segmented electrode 452. The segmented electrodes 552 optionally include one or more additional features to aid in holding the segmented electrode within the lead. One embodiment of a segmented electrode 552 displaying several optional features is provided in FIG. 5. The segmented electrode includes a stimulation surface 584 that, when the lead is formed and inserted into the patient, will be exposed to patient tissue. The segmented electrode also includes an interior surface 586 opposing the stimulation surface 584. The interior surface 566 will be in the interior the lead. One optional feature that aids in anchoring the segmented electrode 552 within the lead is a corrugated, or otherwise rough or non-uniform, texture 588 of the interior surface 586. The non-uniform texture 588 of the interior surface 586 increases the surface area that contacts the material of the lead body that is formed around the segmented electrode 552 and helps in retaining the segmented electrode within the lead. The corrugation of the texture 588 can have a triangular cross-section, as illustrated in FIG. 5, or any other suitable shape including, but not limited, a square, rectangular, trapezoidal, hemispherical, hexagonal, or any other regular or irregular cross-section. Other examples of suitable non-uniform textures include, but are not limited to, a checkerboard arrangement that is similar to corrugation but with intersecting grooves, an arrangement with multiple cleat-like projections or dimples extending from the surface 586, or a surface with a texture formed by knurling, grit blasting, or other methods of roughening of the surface, and the like.

Another optional feature of the segmented electrode 552 is one or more legs 560. The legs 560 are arranged so that they project into the interior of the lead and into the material of the lead body that is formed around the segmented electrode. The legs can have any suitable size or shape and may optionally include one or more holes 592 in the legs. In at least some embodiments, material from the lead body can flow into the holes 592 dining the molding process to provide additional anchoring. When the segmented electrode 552 includes more than one leg 560, the legs can be arranged around the segmented electrode in any suitable arrangement. For example, as illustrated in FIG. 5, two legs 560 can extend from opposing sides towards each other. In other embodiments, the two legs may extend from only a portion of a particular side of the segmented electrode 552. For example, two legs may extend from the segmented electrode 552 with one leg extending near one end of a side of the electrode and the other leg extending near the other end of the opposing side of the electrode so that the two legs are diagonally opposed. It will be understood that other arrangements can be used including, for example, arrangements in which legs are directly opposed.

Figure 6:
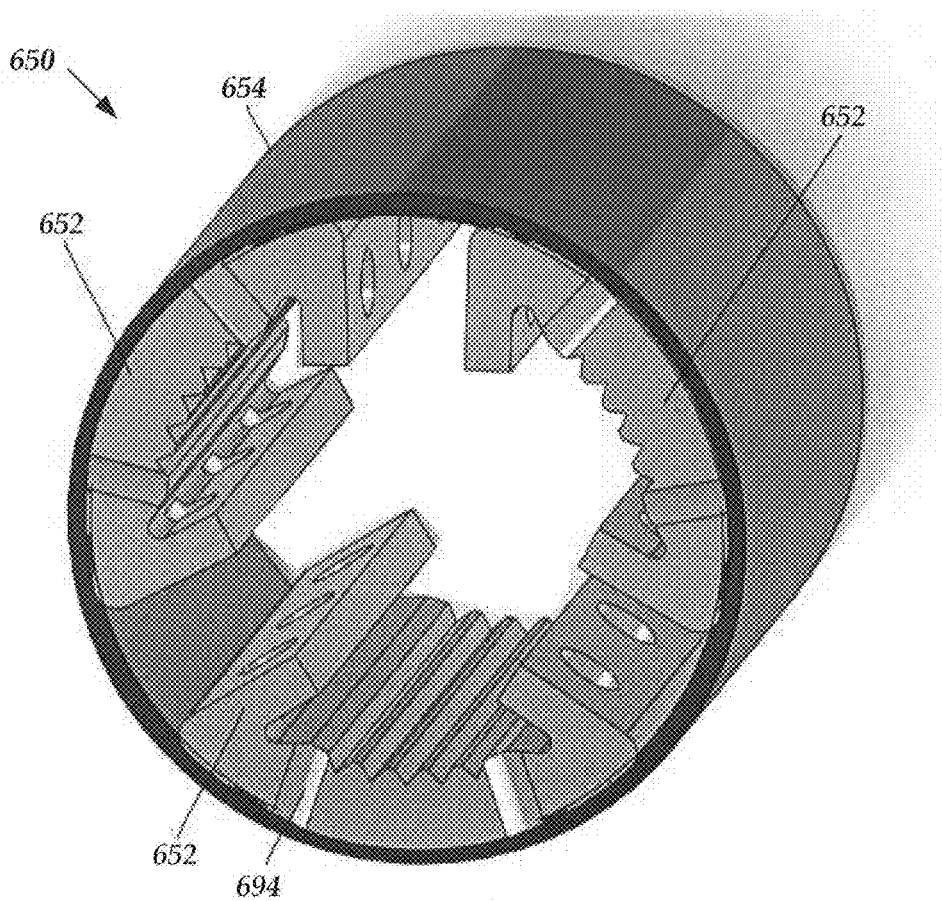
FIG. 6 is a perspective view of a second embodiment of a pre-electrode, according to the invention.

Yet another optional feature of the segmented electrodes is one or more radial channels 694, as illustrated in FIG. 6. These radial channels 694 can be on the edges of the segmented electrode 652, as illustrated in FIG. 6, or be openings through the body of the segmented electrode. These radial channels 694 can facilitate retention of the segmented electrode in the lead body by interacting with the material of the lead body.

Returning to FIG. 4A, at least one conductor wire 466 is coupled to each of the segmented electrodes 452. The conductor wires can be attached using any suitable technique including, but not limited to, welding, soldering, crimping, staking, or the like.

Figure 4B:
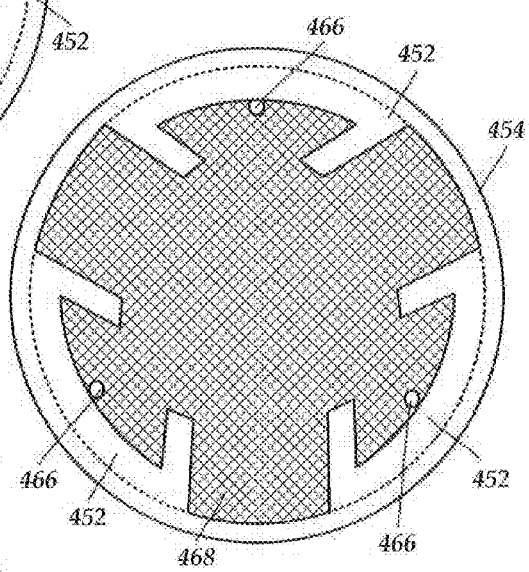
FIG. 4B is a cross-sectional view of the pre-electrode of FIG. 4A with a lead body formed through the pre-electrode, according to the invention.

In the process of lead manufacture, a lead body 468 is formed around the segmented electrodes 452 and conductor wires 466 and through the ring 454, as illustrated in FIG. 4B. The lead body can be formed using, for example, a polymeric material such as polyurethane, silicone, or the like or any combination thereof. It will be understood that there can be more than one pre-electrode 450 with segmented electrodes 452 and that the lead body 468 can be simultaneously formed around all of these segmented electrodes. For example, in at least some embodiments, the pre-electrodes 450 can be placed in a mold in a space-apart arrangement. The material of the lead body 468 can then be formed around the segmented electrodes 452 and through the pre-electrodes 450. The lead body 468 can also pass through the holes 582 (see FIG. 5), if any, of the electrodes 452.

Figure 4C:
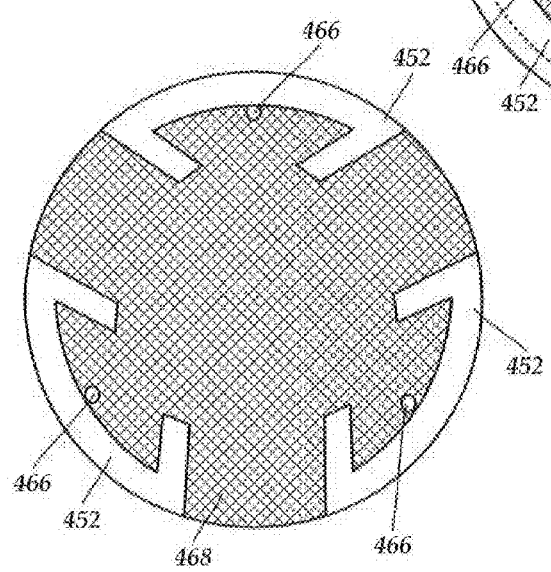
FIG. 4C is a cross-sectional view of the segmented electrodes of the pre-electrode of FIG. 4A released from the ring of the pre-electrode, according to the invention.

After forming the lead body 468, the ring 454 that connects the segmented electrodes 452 together is removed, as illustrated in FIG. 4C. This separates the segmented electrodes 452 and also exposes the outer surface 458 of the segmented electrodes so that outer surface can be used for electrical stimulation of adjacent tissue when the lead is implanted. Any suitable process can be used for removing the ring 454 including, but not limited to, grinding (such as, centerless grinding), ablation, etching, machining, and the like or any combination thereof. In some embodiments, removal of the ring may also include removal of outer portions of the segmented electrodes 452 or lead body 468 or both.

Instead of forming the ring and segmented electrodes in a single, unitary body, the segmented electrodes can be attached to a separate ring. FIG. 6 illustrates an embodiment of a pre-electrode 650 with a separate ring 654 having segmented electrodes 652 attached to the interior of the ring. Such an arrangement can also be used with any of the other embodiments described with respect to FIGS. 7A-8C. Further description of such arrangements of a pre-electrode is presented in U.S. Provisional Patent Application Ser. No. 61/829,912, filed May 31, 2013, incorporated herein by reference.

Figure 7A:
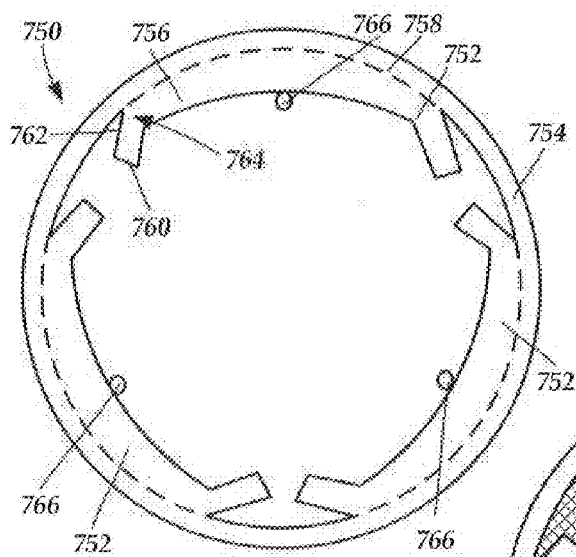
FIG. 7A is a cross-sectional view of a third embodiment of a pre-electrode, according to the invention.
Figure 7B:
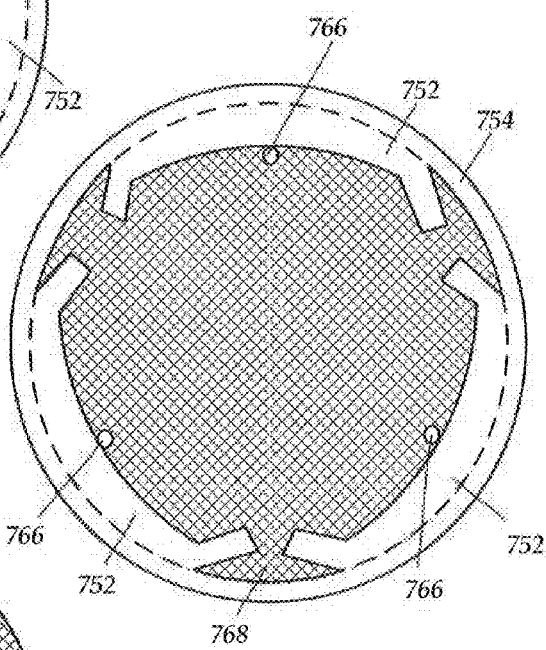
FIG. 7B is a cross-sectional view of the pre-electrode of FIG. 7A with a lead body formed through the pre-electrode, according to the invention.
Figure 7C:
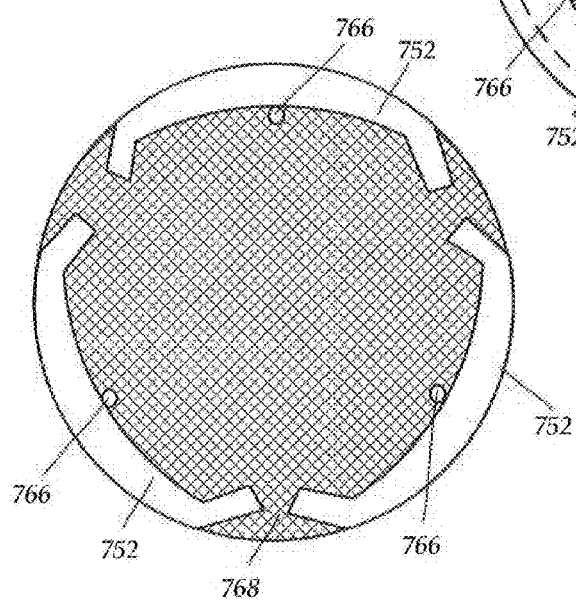
FIG. 7C is a cross-sectional view of the segmented electrodes of the pre-electrode of FIG. 7A released from the ring of the pre-electrode, according to the invention.

In other embodiments, the outer surface of the segmented electrodes forms an obtuse angle with the outer surface of the leg(s). FIGS. 7A-7C illustrates a pre-electrode 750 having multiple segmented electrodes 752 that are connected together by a removable ring 754. Each of the segmented electrodes 752 has an electrode body 756 and one or more legs 760 extending from the electrode body 756. The illustrated embodiment has two legs, but it will be understood that any number of legs can be provided including a single leg.

The electrode body 756 has an outer surface 758 (represented by the dotted lines in FIGS. 7A and 7B) that will be exposed when the ring 754 is removed during manufacture (see FIG. 7C). In addition, each of the legs 760 has an outer surface 762. The outer surface 758 of the electrode body 756 forms an obtuse angle 764 with the outer surface 762 of the leg 760. In at least some embodiments, the obtuse angle is in the range of 95 to 135 degrees or in the range of 100 to 125 degrees. In at least some embodiments, the obtuse angle is at least 95, 100, 105, or 110 degrees. When the segmented electrode has two or more legs, the obtuse angles between the each individual leg and the electrode body can be the same or they can be different.

In addition, in some embodiments, the angle between one or more legs and the electrode body can be acute and the angle between one or more other legs and the electrode body can be obtuse. In other embodiments, one or more legs can be perpendicular to the outer surface of the electrode body and one or more other legs can be non-perpendicular (i.e., forming an acute or obtuse angle) to the outer surface of the electrode body. Additional examples of segmented electrodes, including segmented electrodes that can be modified so that the leg(s) of those segmented electrodes form an obtuse angle with the electrode body, can be found in U.S.

Provisional Patent Application Ser. No. 61/829,918, filed May 31, 2013, incorporated herein by reference.

At least one conductor 766 is attached to each segmented electrodes. During manufacture, a lead body 768 is formed through the pre-electrode 750 and around the segmented electrodes 752 and conductors 766, as illustrated in FIG. 7B. The ring 754 is then removed leaving the segmented electrodes 752, as illustrated in FIG. 7C.

Figure 8A:
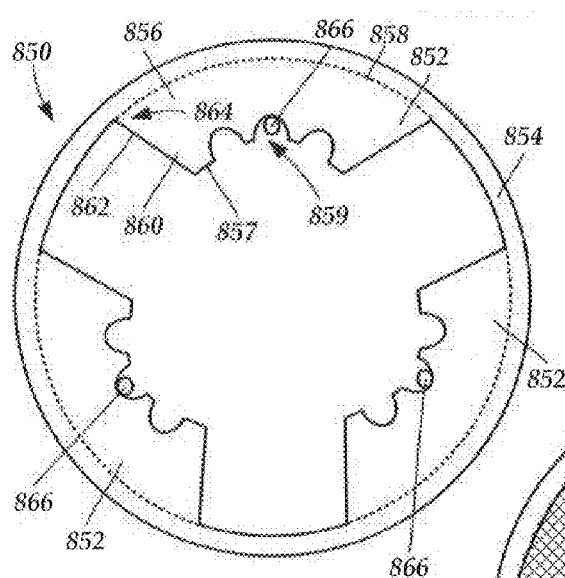
FIG. 8A is a cross-sectional view of a fourth embodiment of a pre-electrode, according to the invention.
Figure 8B:
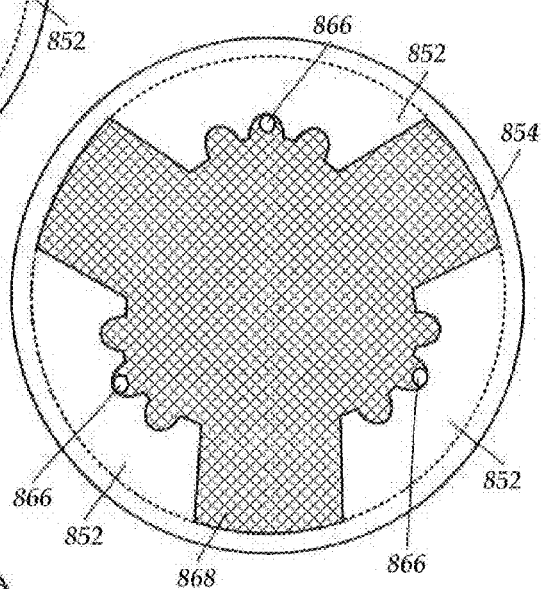
FIG. 8B is a cross-sectional view of the pre-electrode of FIG. 8A with a lead body formed through the pre-electrode, according to the invention.
Figure 8C:
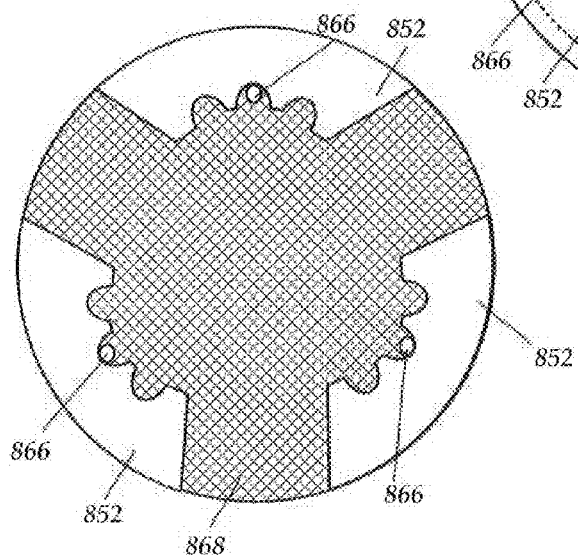
FIG. 8C is a cross-sectional view of the segmented electrodes of the pre-electrode of FIG. 8A released from the ring of the pre-electrode, according to the invention.

In other embodiments, the inner surface of the segmented electrodes defines one or more channels. FIGS. 8A-8C illustrates a pre-electrode 850 having multiple segmented electrodes 852 that are connected together by a removable ring 854. Each of the segmented electrodes 852 has an electrode body 856 and one or more legs 860 extending from the electrode body 856. The illustrated embodiment has two legs, but it will be understood that any number of legs can be provided including a single leg.

The electrode body 856 has an outer surface 858 (represented by the dotted lines in FIGS. 8A and 8B) that will be exposed when the ring 854 is removed during manufacture (see FIG. 8C). In addition, each of the legs 860 has an outer surface 862. The outer surface 858 of the electrode body 856 forms an acute angle 864 (or an obtuse angle) with the outer surface 862 of the leg 860.

The inner surface 857 of the electrode body 856 defines one or more channels 859, as illustrated in FIG. 8A. Other examples of segmented electrodes with channels along the inner surface can be found in U.S. Provisional Patent Application Ser. No. 61/829,918, filed May 31, 2013, incorporated herein by reference. In at least some embodiments, the conductor 866 can be disposed within one of the channels 859.

A conductor 866 is attached to each segmented electrodes. During manufacture, a lead body 868 is formed through the pre-electrode 850 and around the segmented electrodes 852 and conductors 866, as illustrated in FIG. 8B. The ring 854 is then removed leaving the segmented electrodes 852, as illustrated in FIG. 8C.

Figure 9A:
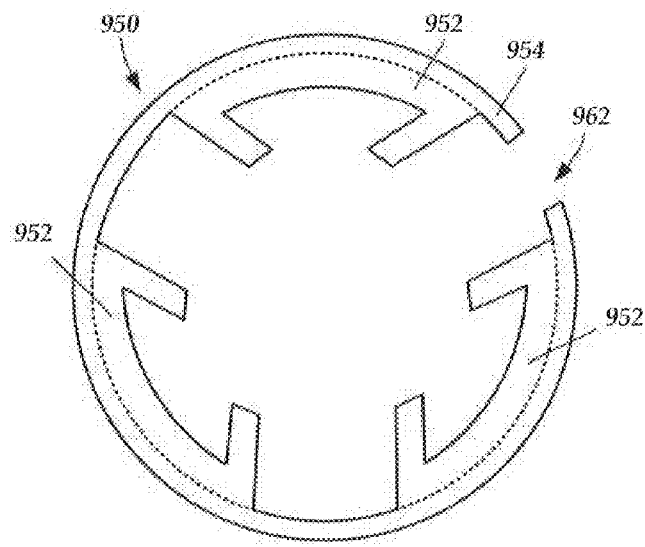
FIG. 9A is a cross-sectional view of a fifth embodiment of a pre-electrode including an opening, according to the invention.
Figure 9B:
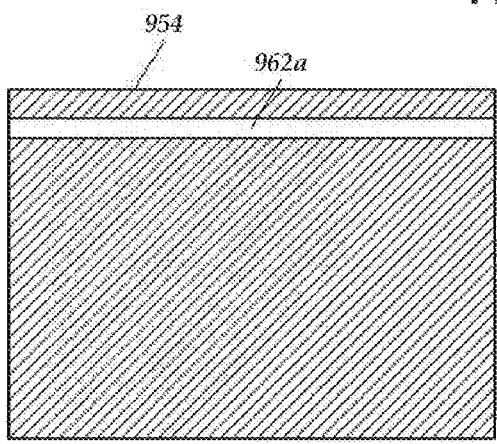
FIG. 9B is a side view of the ring of FIG. 9A where the opening is a slit, according to the invention.
Figure 9C:
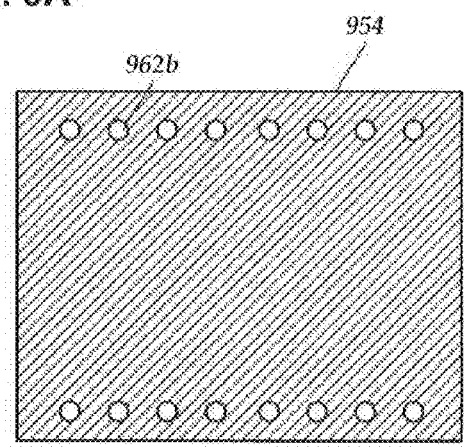
FIG. 9C is a side view of the ring of FIG. 9A where the opening is a set of holes through the ring, according to the invention.

FIGS. 9A-9C illustrated other embodiments of a pre-electrode 950 with a ring 954 with electrodes 952 attached to the interior of the ring. In these embodiments, the ring 950 has at least one opening 962 through the ring. In FIG. 9B, the opening is a slit 962a that can extend the entire axial length of the ring 954 or only a portion of the axial length of the ring. In FIG. 9C, the opening is one or more holes 962b formed through the ring 954. The opening 962 (such as slit 962a or hole 962b) may facilitate manufacture as the material of the lead body may extend into the opening as the lead body is formed which may reduce rotational or axial slippage of the ring during subsequent processing (at least until the ring is removed) and, therefore, reduce the possibility of the placement of the segmented electrodes being altered during that processing.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A pre-electrode, comprising:
    an outer portion; and
    a plurality of separated segmented electrodes distributed around a circumference of the pre-electrode and within the outer portion;
    wherein the pre-electrode is a single, unitary, undifferentiated construct with a ring-shaped exterior and is configured and arranged so that removal of the outer portion results in the remaining portions forming the plurality of separated segmented electrodes, wherein each of the separated segmented electrodes comprises a body and at least one leg extending inwardly from the body, the body defining an external stimulating surface and each of the at least one leg having an outer surface, wherein, for at least one of the at least one leg, the outer surface of the leg forms a non-perpendicular angle with the external stimulating surface of the body, wherein the outer portion and the plurality of segmented electrodes are made of a same conductive material.

2. A method of making an electrical stimulation lead, the method comprising:
    attaching the pre-electrode of claim 1 to a lead body;
    b) attaching a plurality of conductor wires to the pre-electrode; and
    c) after attaching to the lead body, removing the outer portion of the pre-electrode to separate remaining portions of the pre-electrode into the plurality of segmented electrodes spaced around a circumference of the lead body, wherein, for at least one of the at least one leg, the outer surface of the leg forms an acute angle with the external stimulating surface of the body.

3. The method of claim 2, wherein, after removing the outer portion of the pre-electrode, the plurality of segmented electrodes are spaced evenly around the circumference of the lead body.

4. The method of claim 2, wherein removing the outer portion of the pre-electrode comprises grinding the outer portion of the pre-electrode to separate the plurality of segmented electrodes from each other.

5. The method of claim 2, further comprising repeating steps a)-c) for at least one additional pre-electrode.

6. A method of making an electrical stimulation lead, the method comprising:
    a) attaching the pre-electrode of claim 1 to a lead body;
    b) attaching a plurality of conductor wires to the pre-electrode; and
    c) after attaching to the lead body, removing the outer portion of the pre-electrode to separate remaining portions of the pre-electrode into the plurality of segmented electrodes spaced around a circumference of the lead body, wherein, for at least one of the at least one leg, the outer surface of the leg forms an obtuse angle with the external stimulating surface of the body.

7. The method of claim 6, wherein, after removing the outer portion of the pre-electrode, the plurality of segmented electrodes are spaced evenly around the circumference of the lead body.

8. The method of claim 6, wherein removing the outer portion of the pre-electrode comprises grinding the outer portion of the pre-electrode to separate the plurality of segmented electrodes from each other.

9. The method of claim 6, further comprising repeating steps a)-c) for at least one additional pre-electrode.

10. The method of claim 6, wherein the at least one leg is a plurality of legs and wherein, for each of the legs, the outer surface of the leg forms an obtuse angle with the external stimulating surface of the body.

11. The pre-electrode of claim 1, wherein the pre-electrode defines a longitudinal slit along at least a portion of a longitudinal length of the pre-electrode.

12. The pre-electrode of claim 1, wherein the pre-electrode defines a plurality of holes extending from an interior to an exterior of the pre-electrode.

13. The pre-electrode of claim 1, wherein the at least one leg is a plurality of legs and wherein, for each of the legs, the outer surface of the leg forms an acute angle with the external stimulating surface of the body.

14. The pre-electrode of claim 1, wherein the non-perpendicular angle is in a range from 20 to 85 degrees.

15. The pre-electrode of claim 1, wherein the non-perpendicular angle is in a range from 45 to 80 degrees.

16. The pre-electrode of claim 1, further comprising at least one channel formed in an interior surface of the body of at least one of the segmented electrodes.

17. The pre-electrode of claim 1, wherein the non-perpendicular angle is in a range from 95 to 135 degrees.

18. The pre-electrode of claim 1, wherein the non-perpendicular angle is in a range from 110 to 125 degrees.

19. The pre-electrode of claim 1, wherein the at least one leg is a plurality of legs and wherein, for each of the legs, the outer surface of the leg forms an obtuse angle with the external stimulating surface of the body.

* * * * *